US00PP16783P2

(12) United States Plant Patent
Bergman

(10) Patent No.: US PP16,783 P2
(45) Date of Patent: Jul. 11, 2006

(54) ***AZALEA* PLANT NAMED 'CAROUSEL'**

(50) Latin Name: *Rhododendron hybrida*
Varietal Denomination: Carousel

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 38 days.

(21) Appl. No.: 11/119,066

(22) Filed: Apr. 30, 2005

(51) Int. Cl.
*A01H 5/00* (2006.01)

(52) U.S. Cl. ..... Plt./238

(58) Field of Classification Search ..... Plt./238
See application file for complete search history.

*Primary Examiner*—Kent Bell
(74) *Attorney, Agent, or Firm*—C. A. Whealy

(57) ABSTRACT

A new and distinct cultivar of *Azalea* plant named 'Carousel', characterized by its dark green-colored leaves that do not abscise during the cooling and forcing periods; uniform and outwardly spreading plant habit; freely branching habit; uniform and freely flowering habit; relatively rapid flowering response; pale lavender to white-colored flowers with random purple-colored spots and flecks; double to semi-double flower form; and good postproduction longevity with plants maintaining good flower substance for about 25 days in an interior environment.

2 Drawing Sheets

Botanical designation: *Rhododendron hybrida.*
Cultivar denomination: 'Carousel'.

BACKGROUND OF THE INVENTION

The present Invention relates to a new and distinct cultivar of *Azalea*, botanically known as *Rhododendron hybrida*, an evergreen greenhouse-forcing type *Azalea*, and hereinafter referred to by the name 'Carousel'.

The new *Azalea* is a product of a planned breeding program conducted by the Inventor in Alva, Fla. The objective of the breeding program is to create new *Azalea* varieties having uniform plant habit, profuse and uniform flowering response, dark green foliage, good foliage retention during the cooling and forcing periods, resistance to *Cylindrocladium* and excellent postproduction longevity.

The new *Azalea* originated from a cross-pollination made by the Inventor in March, 1996, in Alva, Fla., of a proprietary *Azalea* selection identified as code number YB-1159, not patented, as the female, or seed, parent with a proprietary *Azalea* selection identified as code number YB-1054, not patented, as the male, or pollen, parent. The new *Azalea* was discovered and selected by the Inventor as a flowering plant within the progeny of the stated cross-pollination in a controlled environment in Alva, Fla., in June, 1998.

Asexual reproduction of the new *Azalea* by terminal cuttings taken in a controlled environment in Alva, Fla. since September, 1998, has shown that the unique features of this new *Azalea* are stable and reproduced true to type in successive generations.

SUMMARY OF THE INVENTION

The new *Azalea* has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Carousel'.

These characteristics in combination distinguish 'Carousel' as a new and distinct cultivar:

1. Dark green-colored leaves that do not abscise during the cooling and forcing periods.
2. Uniform and outwardly spreading plant habit.
3. Freely branching habit.
4. Uniform and freely flowering habit.
5. Relatively rapid flowering response; plants begin flowering about 36 days after cooling treatment.
6. Pale lavender to white-colored flowers with random purple-colored spots and flecks.
7. Double to semi-double flower form.
8. Good postproduction longevity with plants maintaining good flower substance for about 25 days in an interior environment.

In side-by-side comparisons conducted in Alva, Fla., plants of the new *Azalea* differed from plants of the female parent selection primarily in flower color as plants of the female parent selection had dark pink-colored flowers.

In side-by-side comparisons conducted in Alva, Fla., plants of the new *Azalea* differed from plants of the male parent selection primarily in flower color as plants of the male parent selection had coral lavender-colored flowers. In addition, plants of the male parent selection had single flowers.

Plants of the new *Azalea* can be compared to the plants of the cultivar Lavender Lace, disclosed in U.S. Plant Pat. No. 11,137. However, in side-by-side comparisons conducted in Alva, Fla., plants of the new *Azalea* differed from plants of the cultivar Lavender Lace in the following characteristics:

1. Plants of the new *Azalea* had darker green-colored leaves than plants of the cultivar Lavender Lace.
2. Plants of the new *Azalea* had double to semi-double flowers whereas plants of the cultivar Lavender Lace had single flowers.
3. Plants of the new *Azalea* and the cultivar Lavender Lace differed in flower coloration.

BRIEF DESCRIPTION OF THE PHOTOGRAPHS

The accompanying colored photographs illustrate the overall appearance of the new *Azalea*. These photographs show the colors as true as it is reasonably possible to obtain in colored reproductions of this type. Colors in the photographs may differ slightly from the color values cited in the detailed botanical description, which accurately describe the colors of the new *Azalea*.

The photograph on the first sheet comprises a side perspective view of a typical flowering plant of 'Carousel'.

The photograph on the second sheet is a close-up view of typical flowers and leaves of 'Carousel'.

DETAILED BOTANICAL DESCRIPTION

The aforementioned photographs and following observations and measurements describe plants grown in Alva, Fla. with three plants per 15-cm containers, in a polypropylene-covered shade house during the winter and early spring and under commercial production conditions. During the production of the plants, day temperatures ranged from 13 to 37° C. and night temperatures ranged from 0 to 26° C. Plants were pinched at planting, pinched a second time about twelve weeks later, and then pinched a third time about twelve weeks after the second pinch. After sufficient flower bud development, plants were cooled at 3 to 5° C. for about four weeks to break flower bud dormancy. Plants were subsequently forced into flower under commercial production conditions in a polyethylene-covered greenhouse. Plants used for the photographs and description were about one year old.

In the following description, color references are made to The Royal Horticultural Society Colour Chart, 1995 Edition, except where general terms of ordinary dictionary significance are used.

Botanical classification: *Rhododendron hybrida* 'Carousel'.

Commercial classification: Evergreen greenhouse-forcing type *Azalea*.

Parentage:

*Female or seed parent*.—Proprietary *Rhododendron hybrida* selection identified as code number YB-1159, not patented.

*Male or pollen parent*.—Proprietary *Rhododendron hybrida* selection identified as code number YB-1054, not patented.

Propagation:

*Type*.—By terminal vegetative cuttings.

*Time to initiate roots*.—Summer: About five weeks at temperatures of 24° C. Winter: About six weeks at temperatures of 24° C.

*Time to develop roots*.—Summer: About nine weeks at temperatures of 24° C. Winter: About eleven weeks at temperatures of 24° C.

*Root description*.—Fine, fibrous, and white in color.

*Rooting habit*.—Freely branching.

Plant description:

*Plant form and growth habit*.—Perennial, evergreen; uniform and outwardly spreading plant habit; broad inverted triangle; moderately vigorous growth habit. Densely foliated. Uniform and freely flowering habit with numerous double to semi-double flowers per plant.

*Branching habit*.—Freely branching; about four primary lateral branches develop after the initial pinch (removal of terminal apex); numerous secondary and tertiary branches develop after the sequential second and third pinches.

*Plant height, soil level to top of flowers*.—About 25 cm.

*Plant diameter, area of spread*.—About 39 cm.

*Lateral branch description*.—Length: About 21 cm. Diameter at base: About 4 mm. Internode length: About 1.75 cm. Strength: Very strong. Texture, young: Pubescent, fine brown hairs. Texture, mature: Woody; pubescent, fine brown hairs. Color, young: Close to 144A. Color, mature: Close to 165A.

*Foliage description*.—Arrangement: Alternate, single. Foliage retention: Very good foliage retention on plants of the new *Azalea* that have been in a box for six weeks during the cooling treatment. Length: About 5.4 cm. Width: About 2.3 cm. Shape: Mostly elliptic. Apex: Cuspidate to mucronate. Base: Attenuate. Margin: Entire. Venation pattern: Pinnate. Texture, upper and lower surfaces: Leathery, tough, durable; pubescent. Color: Developing and fully expanded foliage, upper surface: Darker green than 147A. Developing and fully expanded foliage, lower surface: Close to 147B. Venation, upper surface: Close to 147A; towards the base, close to 146A. Venation, lower surface: Close to 146A to 146C. Petiole: Length: About 9 mm. Diameter: About 2 mm. Texture, upper and lower surfaces: Pubescent. Color, upper and lower surfaces: Close to 146B to 146C.

Flower description:

*Natural flowering season*.—Spring after sufficient cool period. If forced, plants typically flower about 36 days after a four-week cooling treatment; relatively rapid flowering response. Flowers persistent.

*Flower arrangement*.—Flowers arranged singly at terminals with usually about four to five flowers per apex; uniform and freely flowering habit. Flowers face upward to mostly outward. Flowers rotate and somewhat star-shaped.

*Flower appearance*.—Double to semi-double flower form with a outer single whorl of petals and one to two inner whorls of petaloids (transformed stamens); light lavender to white-colored flowers with random purple spots and flecks.

*Fragrance*.—None detected.

*Flower diameter*.—About 6.2 cm.

*Flower depth*.—About 2.7 cm.

*Postproduction longevity*.—Good postproduction longevity; under interior conditions, plants maintain good flower substance for about 25 days.

*Flower bud (before showing color)*.—Length: About 1.5 cm. Diameter: About 5 mm. Shape: Ovoid. Color: Close to 146B.

*Petals/petaloids*.—Arrangement: Double to semi-double flower form; one outer whorl of about five imbricate petals and one to two inner whorls each with about five imbricate petaloids (transformed stamens); petals and petaloids fused at the base. Petaloids variable in size and shape. Length, petals: About 4.2 cm. Width, petals: About 2.6 cm. Length, petaloids, center whorl: About 3.8 cm. Width, petaloids, center whorl: About 2.5 cm. Length, petaloids, inner whorl: About 2.8 cm. Width, petaloids, inner whorl: About 1.5 cm. Shape, petals and petaloids: Beyond fused base, roughly spatulate with rounded apex. Margin, petals and petaloids: Entire; undulate. Texture, petals and petaloids, upper and lower surfaces: Smooth, glabrous; velvety.

Color, petals and petaloids: When opening and fully opened, upper surface: Close to 75D to 155D; random spots and streaks, close to 77A; central spots, close to 75A. When opening and fully opened, lower surface: Close to 75D to 155D; random spots and flecks, close to 77A.

*Sepals*.—Arrangement: Five in a single whorl, fused; subtending the petals. Length: About 9 mm. Width: About 5 mm. Shape: Lanceolate. Apex: Acute. Texture, upper and lower surface: Pubescent. Color, upper surface: Close to 144A. Color, lower surface: Close to 146A.

*Peduncles*.—Length: About 1.7 cm. Diameter: About 2 mm. Angle: Mostly upright. Strength: Flexible; strong. Texture: Very pubescent. Color: Close to 144A.

*Reproductive organs*.—Androecium: None observed, typically all stamens transferred into petaloids. Gynoecium: Quantity of pistils per flower: One; pistils distorted and flattened. Pistil length: About 9 mm. Style length: About 6 mm. Style color: Close to 144A. Stigma shape: Rounded. Stigma diameter: Less than 1 mm. Stigma color: Close to 144A. Ovary color: Close to 147A; heavily whiskered.

*Seed/fruit*.—Seed and fruit development have not been observed.

Weather/temperature tolerance: Plants of the new *Azalea* have been observed to be very tolerant to rain and wind. Plants of the new *Azalea* have been observed to tolerate temperatures from 0 to 38° C.

Disease/pest resistance: Plants have not been observed to be resistant to pathogens and pests common to *Azaleas*.

It is claimed:

1. A new and distinct *Azalea* plant named 'Carousel', as illustrated and described.

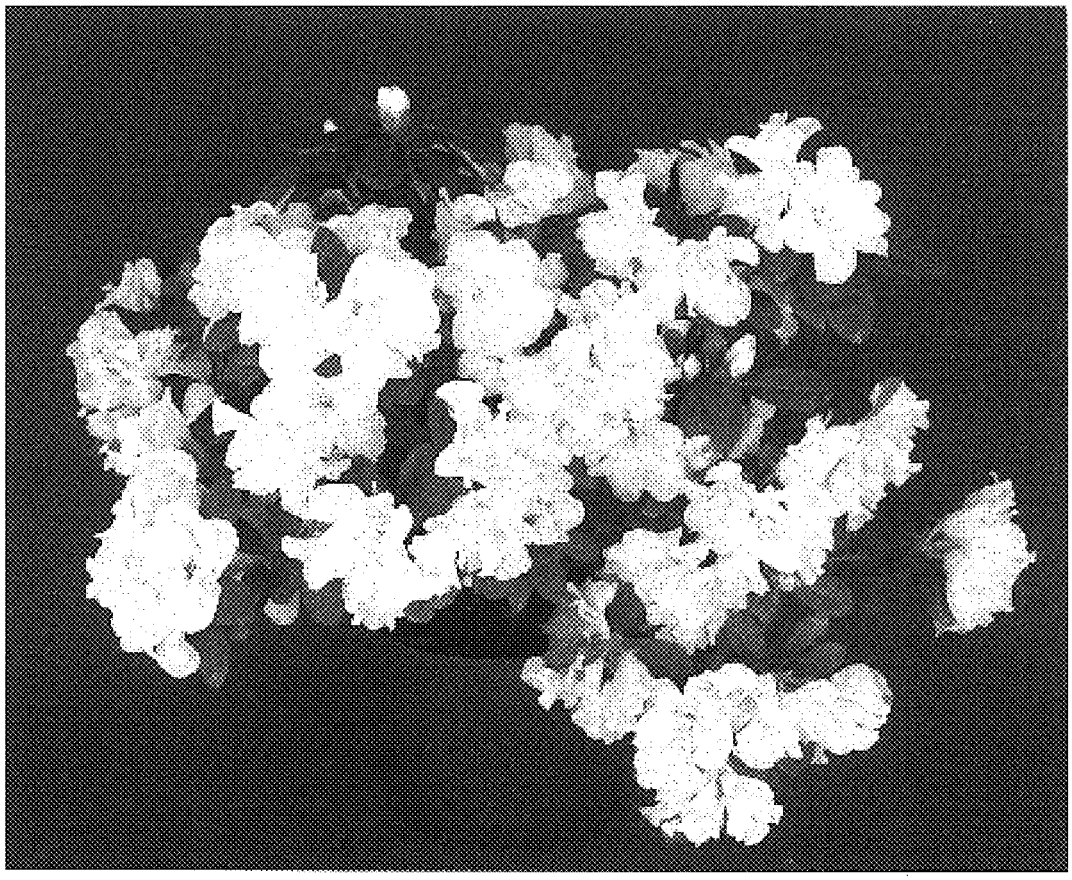

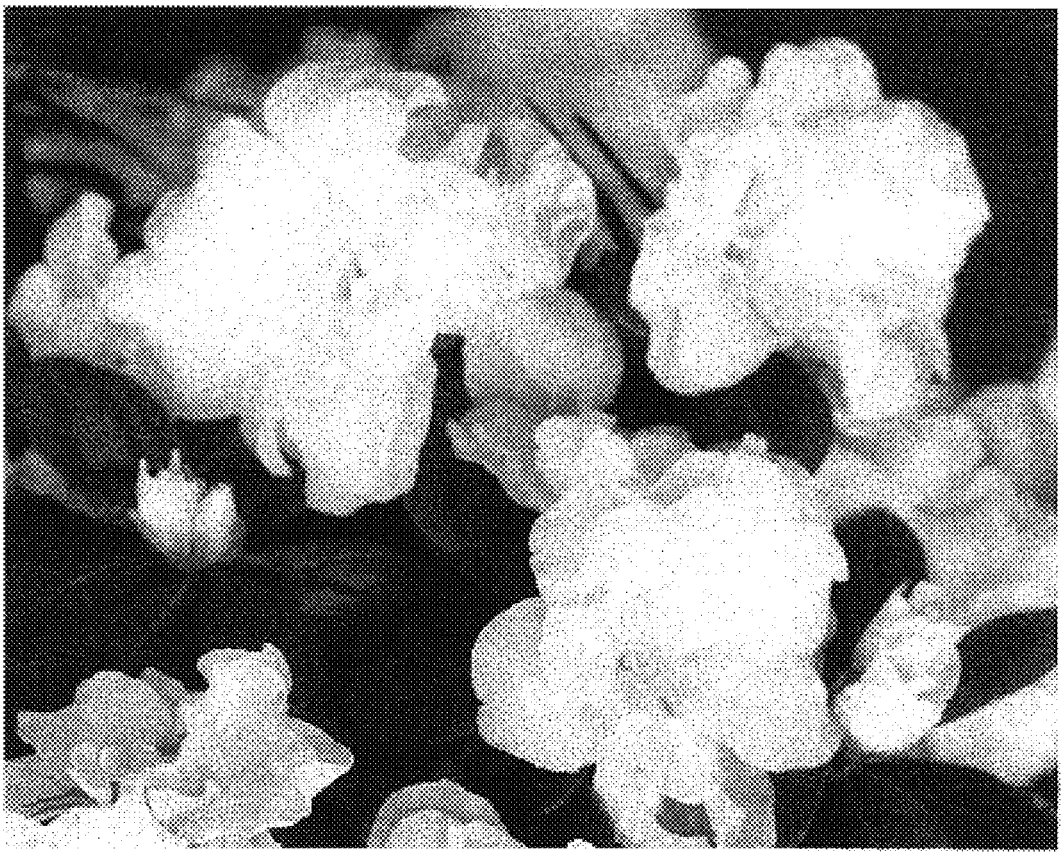

* * * * *